United States Patent [19]

Hirose et al.

[11] 4,064,437

[45] Dec. 20, 1977

[54] METHOD FOR MEASURING THE DEGREE OF ALLOYING OF GALVANNEALED STEEL SHEETS

[75] Inventors: Yusuke Hirose, Ichikawa; Fumihiro Ida, Funabashi; Takehiko Ito, Kamagaya, all of Japan

[73] Assignee: Nisshin Steel Co., Ltd., Tokyo, Japan

[21] Appl. No.: 710,862

[22] Filed: Aug. 2, 1976

[30] Foreign Application Priority Data

Aug. 12, 1975    Japan ................................ 50-97141

[51] Int. Cl.² ............................................ G01N 23/20
[52] U.S. Cl. ................................. 250/273; 250/272
[58] Field of Search ............... 250/272, 273, 252, 274

[56] References Cited

U.S. PATENT DOCUMENTS

| 2,926,257 | 2/1960 | Friedman | 250/273 |
| 3,409,774 | 11/1968 | Dykeman | 250/273 |
| 3,417,243 | 12/1968 | Hill | 250/273 |
| 3,843,884 | 10/1974 | Evans | 250/272 |

*Primary Examiner*—Alfred E. Smith
*Assistant Examiner*—B. C. Anderson
*Attorney, Agent, or Firm*—Fleit & Jacobson

[57] ABSTRACT

Highly reliable measurement of degree of alloying of galvannealed steel sheets is carried out in order to fully control the continuous hot-dip galvanizing and galvannealing process on the basis of evaluation of a combination of two or more X-ray diffraction characteristics. Exact degree of alloying can be estimated without regard to fluctuations in the particulars of the material, the process conditions and the type of the product obtained.

9 Claims, 6 Drawing Figures

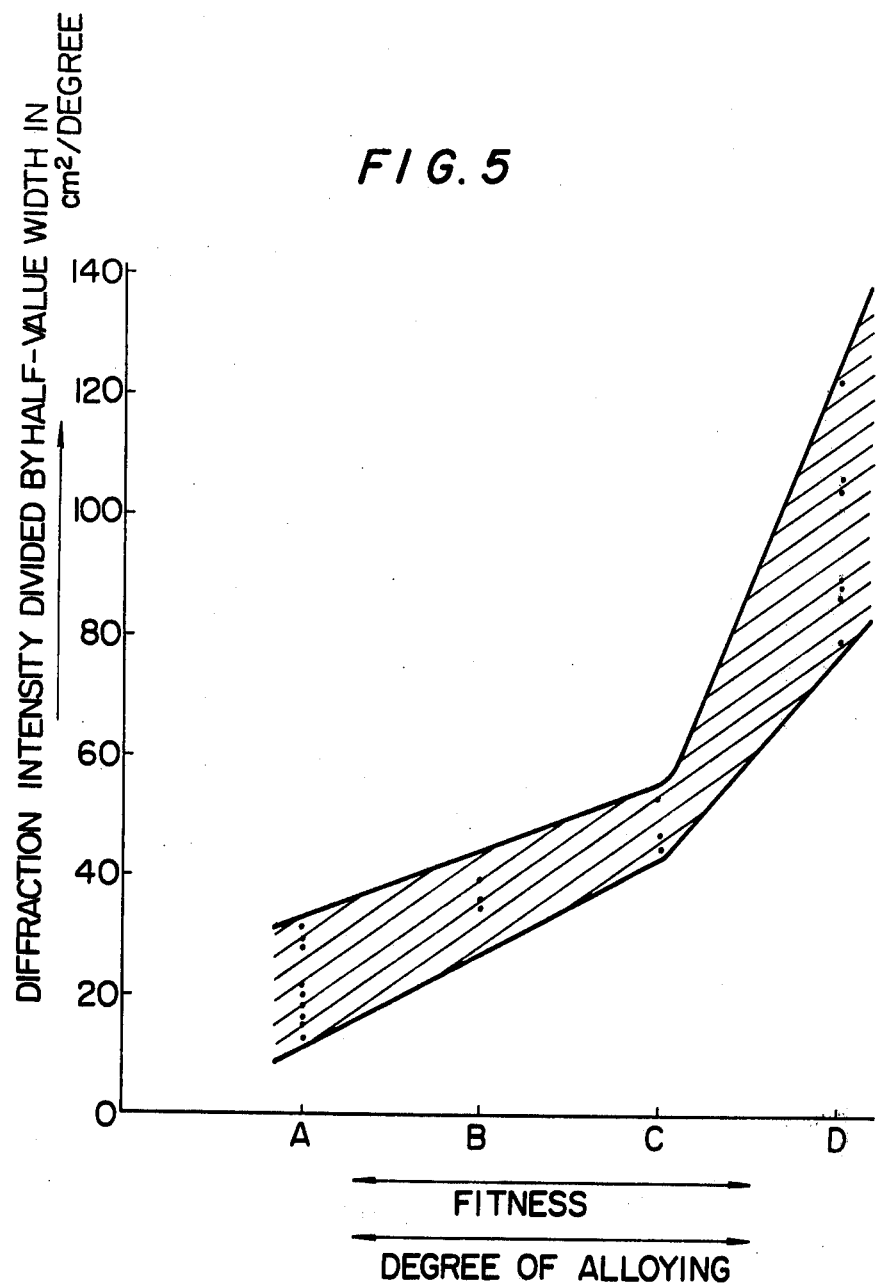

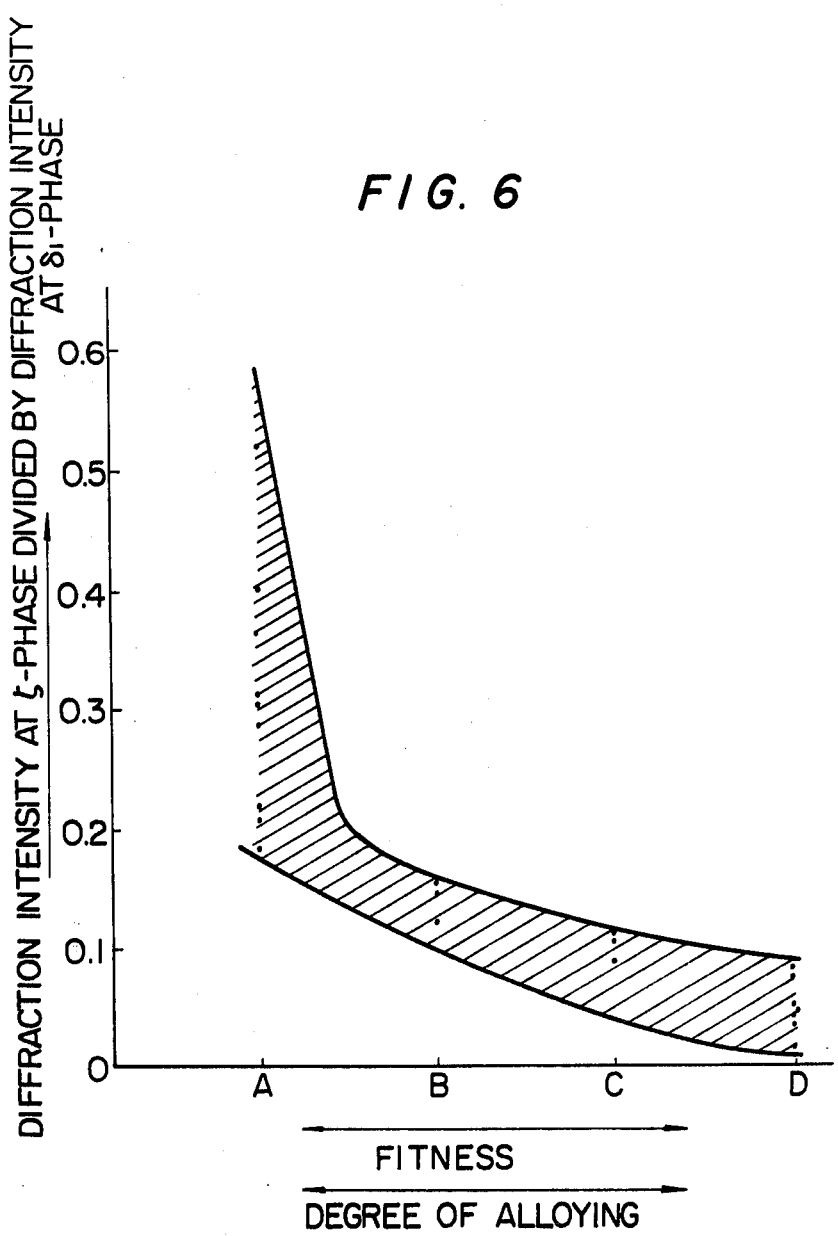

METHOD FOR MEASURING THE DEGREE OF ALLOYING OF GALVANNEALED STEEL SHEETS

BACKGROUND OF THE INVENTION

The present invention relates to a method for measuring the degree of alloying of galvannealed steel sheets and more particularly to a method of a non-destructive, continuous and qualitative measurement of degree of alloying of galvannealed steel sheets through the X-ray diffraction technique.

For the purpose of improving the characteristics of hot-dip galvannealed steel sheets to painting, paint adhesion and welding, a great deal of research work has been conducted on the nature of galvannealed steel sheets in which, through application of heating before solidification of the zinc surface layer just after galvanizing, mainly $\delta_1$-and/or $\zeta$-phase is grown in the galvanized layer.

As a result of the research work, it is now known that the qualitative characteristics of the galvannealed steel sheets is greatly dependent upon the degree of alloying, i.e. the degree of mutual diffusion between iron and zinc.

When the application of heat to the coating just after the hot-dip galvanizing is insufficient, the $\eta$-phase remains in the surface layer and this leads to poor paintability, paint adhesion and welding. Whereas, when the heat application is excessive, overfull diffusion of iron into the zinc coated layer occurs and this lowers fitness of the coated layer to other treatments and resistance of the plated layer against corrosion. Therefore, in order to produce galvannealed steel sheets with excellent quality, it is indispensable to properly control the galvannealing process on the basis of a continuous measurement of the degree of alloying and to keep it within a prescribe range.

In case galvannealed steel sheets are produced by the continuous hot-dip galvanizing process, the degree of alloying is dependent upon various factors such as the thickness of the galvanized steel sheet, the quantity of the coated zinc, the composition of the base steel, the change in the composition of the zinc bath, particularly the change in the aluminum concentration, the heating rate, the maximum heating temperature, the evenness in heating at that temperature, the cooling rate and the variation in the heating atmosphere.

For example, it is required to employ a high heating temperature and a long treatment period when the thickness of the galvanized steel sheet and the quantity of the coating are large. In this connection, however, it is extremely difficult to produce galvannealed steel sheets with proper degree of alloying by adjusting the temperature of the heating furnace and the processing speed only by visual check, as degree of alloying is dependent not only upon the heating temperaturre and period but also upon other factors which influence each other in very complicated ways.

In order to measure the degree of alloying of galvannealed steel sheets, a method has been conventionally and to a major degree employed to detect the change of surface colour tone after the heat application by a direct optical observation or to determine the degree of alloying on the basis of the change of colour tone detected by a photometer. In this measurement system, it is very difficult even for a skilled operator to distinguish delicate and slight change in the colour tone exactly and this difficulty in the practical measurement often causes production of galvannealed steel sheets of somewhat low quality. This is also the case when measuring the degree of alloying by the photometer.

Even in case of products processed under the same heating conditions, reflexibility of light from the surface of galvannealed steel sheets fluctuates from product to product depending upon the type of the base steel, the variation in the zinc bath composition, the heating atmosphere and presence of stains on the surface of galvannealed steel sheets. Such a fluctuation in the reflexibility of light leads to lowered reliability of the measurement.

In addition, no available direct information as to the state of the iron-zinc intermetallic compound in the galvannealed layer can be obtained through the measurement by the direct optical observation of the colour tone of the galvannealed surface and the measurement by detection of the reflexibility of light. Thereby in the case of these measurement systems used for evaluation of the degree of alloying of the galvannealed steel sheets, criteria need to be changed in accordance with variation in the quantity of the coating. Thus, the measurement systems based on the colour tone and the reflexibility of light are not recommended for use in connection with a practical continuous galvannealing process.

For example, a galvannealed steel sheet of good quality may be obtained with the reflexibility ranging from 30 to 35% when the quantity of the coating on one side is $60gr/m^2$. However, the same range of the reflexibility does not always assure the production of a galvannealed steel sheet with the same good quality when the quantity of the coated zinc is $90gr/m^2$. At this range of the reflexibility with the above-mentioned quantity of the coated zinc, the degree of alloying is too high, and thereby the ductility of the coating and the resistance against corrosion are seriously degraded.

Thus, it will be readily understood that it is extremely difficult to successfully avoid production of galvannealed steel sheets of degraded quality in the continuous hot-dip galvanizing and galvannealing process when the degree of alloying is measured by the conventional optical observation of the colour tone and the photometer detection of the reflexibility. Particularly, in consideration of the recent trend in which there is a strong demand for galvannealed steel sheets with a large quantity of coated zinc, e.g. a galvannealed steel sheet of a quantity of coated zinc exceeding $120gr/m^2$ on one side, the conventional systems for measuring the degree of alloying being unsatisfactory to minimize unacceptable production of galvannealed steel sheets with unacceptablly degraded quality.

SUMMARY OF THE INVENTION

It is therefore the object of the present invention to provide a novel method for measurement of the degree of alloying of galvannealed steel sheets which assures highly reliable measurement results regardless of variations in the thickness of sheets, the quantity of the coated zinc, the composition of the base steel, the composition of the zinc bath, the heating rate, the maximum heating temperature, the evenness in heating at the maximum temperature, the cooling rate, the heating atmosphere and the presence of stains on the surface of galvannealed steel sheets.

In accordance with the present invention, measurement is made of at least one of the X-ray diffraction characteristics, i.e., the intensity, the width and the peak angle of the X-ray diffraction profile, of the iron-zinc intermetallic compound of the galvannealed steel sheets and evaluation is made with reference to one of these characteristics or a combination of two or more of the X-ray diffraction characteristics mentioned above.

BRIEF DESCRIPTION OF THE DRAWING

Further features and advantages of the present invention will be made clearer from the ensuing description, reference being made to the accompanying drawings, in which:

FIG. 5 is a graph showing the relationship between the intensity divided by the half-value width of the X-ray diffraction profile and the ductility of the coating, the vertical axis representing the diffraction intensity divided by the half-value width in cm.$^2$/ degree, the upper horizontal axis representing fitness, and the lower horizontal axis representing the degree of alloying; and FIG. 6 is a graph showing the relationship between the X-ray diffraction intensity at $\zeta$-phase divided by that at $\delta_1$-phase and the ductility of the coating, the vertical axis representing the diffraction intensity at $\zeta$-phase divided by the diffraction intensity at $\delta_1$-phase in cm.$^2$/cm.$^2$, the upper horizontal axis representing fitness, and the lower horizontal axis representing the degree of alloying.

DESCRIPTION OF THE PREFERRED EMBODIMENT

Figure 1:
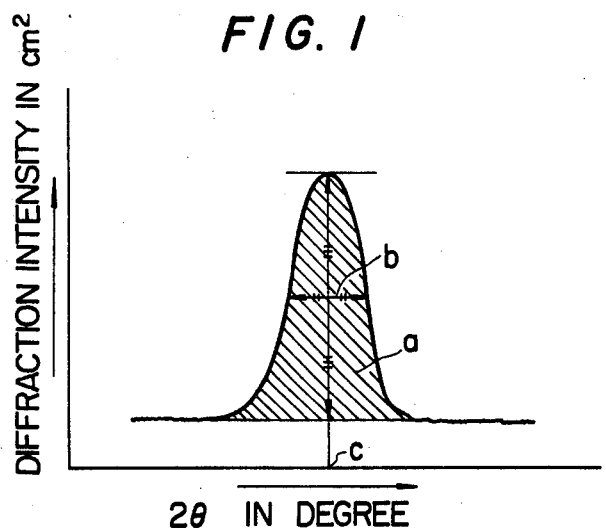
FIG. 1 is a graph showing the X-ray diffraction characteristics of the iron-zinc intermetallic compound of the galvannealed steel sheet, the vertical axis representing the diffraction intensity in cm.$^2$ and the horizontal axis representing $2\theta$ in degrees.

The basic concept of the present invention is based on the correlation between the X-ray diffraction characteristics of the iron-zinc intermetallic compounds of the $\zeta$-phase (FeZn$_{13}$), the $\delta_1$-phase (FeZn$_7$) and the $\Gamma$-phase (Fe$_3$Zn$_{10}$) in the galvannealed coating and the ductility of the coating. The nature of the iron-zinc intermetallic compound is measured by X-ray diffraction technique and the measured result is used to evaluate the degree of alloying of the galvannealed steel sheets.

It was confirmed by the inventors of the present invention that the intensity, the width and the peak angle of the X-ray diffraction profile on a selected crystal plane of an iron-zinc intermetallic compound change as the mutual diffusion advances between iron and zinc and that these X-ray diffraction characteristics exactly reflect the degree of alloying of the galvannealed steel sheets. On the basic of this knowledge, it is intended in accordance with the present invention to utilize this novel measurement system in the production and/or check process of the continuous production of the galvannealed steel sheets.

The physical significances of the above-mentioned X-ray diffraction characteristics of the iron-zinc intermetallic compounds are as follows:

1. X-ray Diffraction Intensity

This factor indicates the quantity of the iron-zinc intermetallic compounds in the galvannealed steel sheet to be measured. It is confirmed that, within the range of the ordinary heating of the galvannealed steel sheet, the crystal orientation in the iron-zinc intermetallic compounds is constant and is not influenced by the heating conditions at all.

2. Width of X-ray Diffraction Profile

This factor indicates the degree of crystal perfection of the iron-zinc intermetallic compounds in the galvannealed steel sheet to be measured.

3. Peak Angle of X-ray Diffraction Profile

This factor corresponds to the crystal interplanar spacings of the iron-zinc intermetallic compounds of the galvannealed steel sheet to be measured. The iron-zinc intermetallic compounds are all non-stoichiometric. Therefore, the composition of the iron-zinc inter-metallic compounds changes with increase in the mutual diffusion between iron and zinc, even though the crystal structure of the compounds remains unchanged. The composition changes so as to contain increased iron share. Thus the degree of alloying can be estimated in reference to the peak angle of the X-ray diffraction profile.

As the X-ray to be used in the present invention, the para-focusing X-ray beam used in the ordinary diffraction method is preferably recommended. However, in the case of the continuous galvanizing and galvannealing process in which the sheets are transported in vibrating condition, it is rather recommended to use the parallel X-ray beam in order to minimize the setting error in the X-ray diffraction system. As for the iron-zinc compounds of the galvannealed steel sheets to be measured, measurement may be applied to one or two or more of the $\zeta$-phase, the $\delta_1$-phase and the $\Gamma$-phase. In general, it is sufficient to measure either one of the $\zeta$-phase and the $\delta_1$-phase.

In accordance with the present invention, there is no special limitation to the crystal lattice plane to which the measurement should be applied. When it is confirmed that the galvannealed coating has a definite crystal orientation, it is sufficient to apply the measurement to one crystal lattice plane only. In order to enchance the accuracy of the measured results, it is recommended that there be employed as large a diffraction profile angle as possible regardless of the wave length of the X-ray beam. It is more preferable to use the crystal lattice plane having a $2\theta$ value of 80° or larger as the diffraction plane.

The following examples are illustrative of the measurement of the degree of alloying of the galvannealed steel sheet in accordance with the present invention but are not to be construed as limiting same. Particulars of the conditions in the X-ray diffraction, the method for measuring the X-ray diffraction characteristics and method for testing the ductility of coating as an index of the degree of alloying in the following examples are as follows:

(1) Conditions in the X-ray diffraction.

| | |
|---|---|
| (i) Target | cobalt |
| Filter | iron |
| Tube voltage | 35KV. |
| Tube current | 20mA. |
| (ii) X-ray | para-focusing X-ray beam |
| (iii) Divergence slit | 1 degree |
| Receiving slit | 0.15 mm. |
| Time constant | 8 seconds |
| Full scale | 1000 cps (equivalent to 230 mm. length on the chart) |
| Detector | scintillation counter |
| (iv) Scanning speed | ¼ degrees/min. |
| Chart speed | 20 mm./min. |
| (v) The intermetallic compound to be measured and its crystal interplanar spacing* | |

$\delta_1$-phase (FeZn$_7$), (103) lattice plane, 1.28 A (approximate)
The peak angle of the diffraction profile (2θ);88.6∼89.0 degree

*Note: for the case shown in Fig. 6, the lattice plane of about 1.26 A spacing of the δ-phase was subjected to the measurement in addition to the above-listed $\delta_1$-phase compound. The Miller index could not be identified. The peak angle (2θ) of the X-ray diffraction profile then was in the range from 90.2 to 91.0 degrees.

2. Method for Measuring the X-ray Diffraction Characteristics

On the basic of the measurement under the above-described conditions, the diffraction intensity "a," the diffraction profile width "b" and the diffraction profile peak angle "c" are obtained in reference to the result shown in FIG. 1. The half-value width is used as the index for the diffraction profile width.

3. Method for Testing the Ductility of the Coating

After bending a galvannealed steel sheet over about 180°, the sheet is returned to its original flat disposition. The portion of the coating subjected to the compressive stress is observed by a magnifying glass of 20 magnifications in order to judge the quality in accordance with the following criteria.

Grade A: No change.
Grade B: Fine Cracks.
Grade C: Big cracks with partial powdering.
Grade D: Big cracks with serous powdering or flaking.

In the ductility of the coating, the degree of alloying of a galvannealed steel sheet of grade A level is higher than that of grade B level, that of grade B level is higher than that of grade C level, and that of grade C level is higher than that of grade D level. So, as a practical matter, the galvannealed steel sheets of grade C and D are degraded products.

Example

The galvannealed steel sheets used as the test piece of the particulars listed in the following Table 1 are produced by the continuous galvanizing and galvannealing process of the Sendzimir type in order to determine the relationship between the X-ray diffraction characteristics and the ductility of the coating as an index for the degree of alloying. The relationship between the diffraction intensity and the ductility is shown in FIG. 2, that between the half-value width of the diffraction profile and the ductility is shown in FIG. 3 and that between the peak angle of the diffraction profile and the ductility is shown in FIG. 4

Table 1

| Test pieces (22 kinds in total) | |
|---|---|
| Sheet thickness in mm. | 0.45∼0.80 |
| Coating weight of zinc on one side in gr./m² | 30∼90 |
| Base steel | extremely low carbon rimmed steel |
| Zinc bath | 0.14∼0.18 wt.% Al |
| Temperature in the heating in ° C | max. 750∼800 (gas heating) |
| Length of the furnace in m. | 30 |
| Processing speed in m./min. | 50∼100 |

Figure 2:
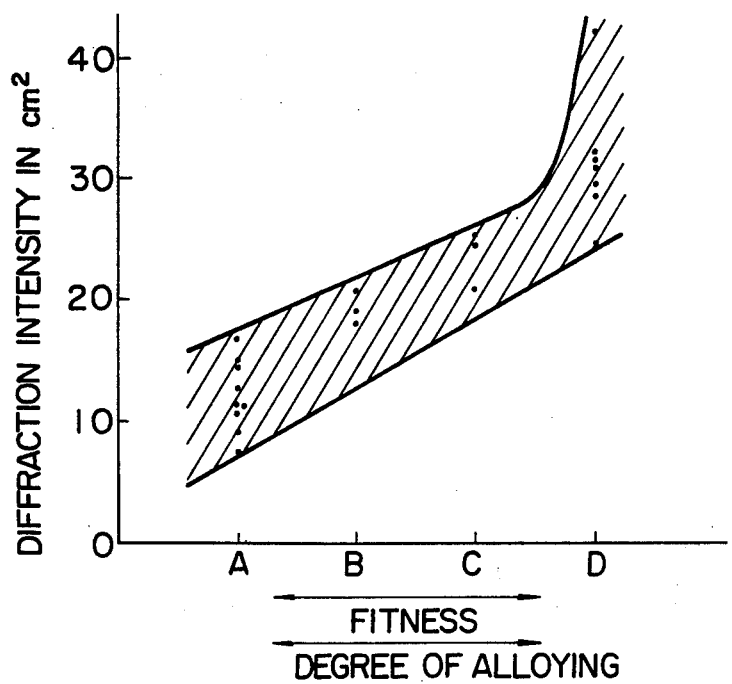
FIG. 2 is a graph showing the relationship between the X-ray diffraction characteristics and the ductility of the coating, the vertical axis representing the diffraction intensity in cm.$^2$, the upper horizontal axis representing fitness, and the lower horizontal axis representing the degree of alloying.
Figure 3:
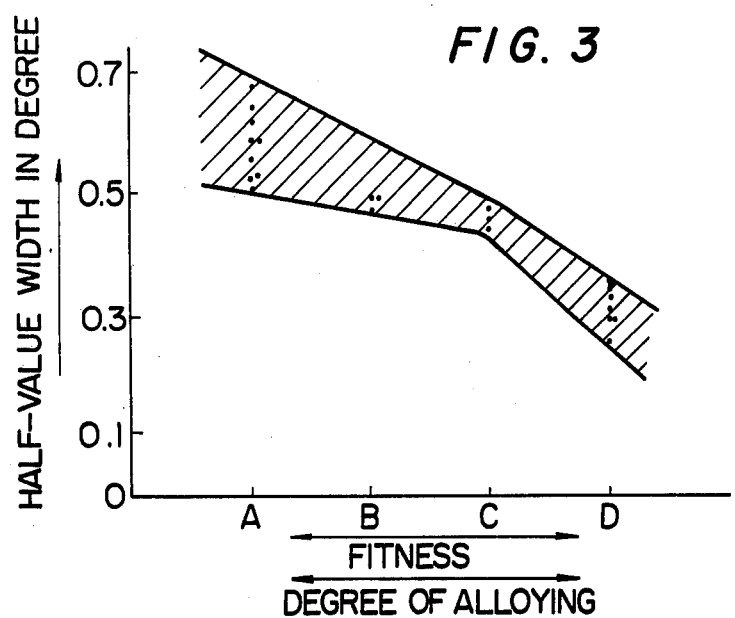
FIG. 3 is a graph showing the relationship between the half-value width of the X-ray diffraction profile and the ductility of the coating, the vertical axis representing the half-value width in degrees, the upper horizontal axis representing fitness, and the lower horizontal axis representing the degree of alloying.
Figure 4:
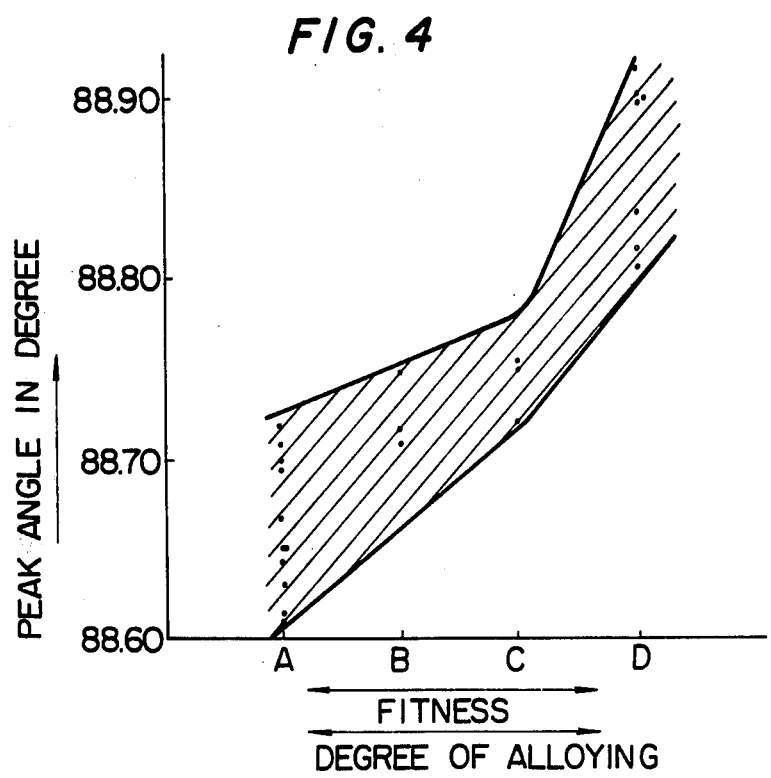
FIG. 4 is a graph showing the relationship between the peak angle of the X-ray diffraction profile and the ductility of the coating, the vertical axis representing the peak angle in degrees, the upper horizontal axis representing fitness, and the lower horizontal axis representing the degree of alloying.

As is learned from the results shown in FIGS. 2 through 4, it is confirmed that a clear correlation exists between the ductility of the coating of the galvannealed steel sheet, i.e., the degree of alloying of the coating, and the X-ray diffraction characteristics thereof. Taking the relationship shown in FIG. 2 between the diffraction intensity and the ductility of the coating in the galvannealed steel sheet as an example, it is necessary to keep the diffraction intensity in the range from 5 to 15 cm.² in order to obtain the ductility of grade A level. When the diffraction intensity exceeds 20cm.², the ductility of the coating is degraded to C or D levels. This shows that the degree of alloying is excessive. When the diffraction intensity falls short of 5cm.², the degree of alloying is insufficient and the paint adhesion is too poor.

When the coating weight is constant, estimation of the alloying can almost be sufficiently attained by measuring only one of the X-ray diffraction characteristics shown in FIGS. 2 through 4, i.e., the diffraction intensity, the diffraction profile width and the diffraction profile peak angle. However, in practice, it is recommended that two or more diffraction characteristics be measured and that the estimation be carried out on the basis of a combination of the results obtained in order to assure a high level of measurement accuracy. In addition, when such a combination is utilized, the degree of alloying can be estimated quantitatively as the influence on the X-ray diffraction characteristics by possible fluctuations in the coating weight can be eliminated.

For example, the diffraction intensity and the diffraction profile width, i.e., the half-value width of the diffraction profile, are measured and the relationship between an index (diffraction the intensity divided by the half-value width of the diffraction profile) and the ductility of the coating is obtained as shown in FIG. 5. In reference to this graph, the degree of alloying can be estimated with enhanced accuracy. Namely, a galvannealed steel sheet having excellent ductility and paint adhesion can be obtained when the degree of alloying is so controlled that the index (the diffraction intensity divided by the half-value width of the diffraction profile) falls in a range 10 to 35 cm.²/degree. Further, by combining this result with the diffraction intensity or with the half-value width of the diffraction profile, the genuine degree of alloying can well be estimated without any influence caused by the fluctuation of the coating.

Similar results can be obtained by applying simultaneous measurements of X-ray diffraction characteristics to two or more iron-zinc intermetallic compounds in the galvannealed steel sheet. That is, the X-ray diffraction characteristics of two or more intermetallic compounds are measured and the degree of alloying is estimated on the basis of the combination of the measured results. Thus, quantitative estimation of the genuine degree of alloying can be obtained in accordance with the ductility of the coating of the galvannealed steel sheet without any influence by fluctuations in the coating weight deposited on the steel sheet. For example, the X-ray diffraction measurements are applied to the intermetallic compounds of $\zeta$-phase and $\delta_1$-phase and the relationship between the intensity ratio, i.e., the ratio of the diffraction intensity with the $\zeta$-phase to that with the $\delta_1$-phase, and the fitness is shown in FIG. 6. From to this graph, it will be well understood that the degrees of alloying of the galvannealed steel sheets of different quantities of deposited zinc can be quantitatively estimated.

It is clear from the foregoing explanation that, in the method of the present invention for measuring the degree of alloying of galvannealed steel sheets, the degree of alloying of galvannealed steel sheets is measured in a non-destructive and quantitative manner. Employment of the present invention using the X-ray diffraction technique in the manufacturing of checking processes of galvannealed steel sheets provides the following advantages.

1. For example, in a continuous hot-dip galvanizing process of the Sendizimir type for production of galvannealed steel sheets, it is possible to carry out successfully the on-line type quantitative measurement of degree of alloying which fluctuations are influenced by the base steel and heating factors. The X-ray diffraction profile width which attains the above object provides not only half-value width but also the width of from ⅓ to 1/5 according to the needs of accuracy. In addition, the measured results can be fed back to the production process in order to properly control the process conditions so that galvannealed steel sheets of remarkably enhanced quality can be produced with a high degree of efficiency in the process.

2. As it is possible to have variable information on the degree of alloying at any time in the production line, production of galvannealed steel sheets of unacceptably low quality can be readily prevented and adjustment of the process conditions can be exactly, quickly, and easily carried out.

3. As the degree of alloying caused by heating can be quantitatively grasped, it is possible, in the case of a relatively lighter coating weight under 100gr./m.² per one side, to obtain a good ductile coating in a high yield.

In addition, products having enhanced fitness to other mechanical treatments such as press forming, can be obtained in high yield. Further, in the case of galvannealed steel sheets having higher coating weights over 120gr./m.² per one side, there is no lowering in paint adhesion caused by poor heating. Further, the products obtained in accordance with the present invention are quite free of lowering of the ductility of the coating and in the resistance against corrosion caused by excessive heating while the yield is very high.

As is already explained in detail, in the process in accordance with the present invention, the degree of alloying of galvannealed steel sheets can be quantitatively, undestructively, and continuously measured by the X-ray diffraction technique in the continuous hot-dip galvanizing and galvannealing line and checking processes.

So, when the present invention is applied to the producing process, production of degraded products can be effectively prevented by instantly adjusting the process conditions in reference to the measured results. Whereas, when the present invention is applied to the checking process, evaluation of the products can be carried out exactly, quickly and easily. Thus, the present invention well contributes to the development of industry, science and technology. Having fully described the novel method of the present invention, methods for measuring and using them and their utility, it is desired that this invention be limited only by the spirit and scope of the following claims.

What is claimed is:

1. The method for measuring the degree of alloying of galvannealed steel sheets comprising measuring at least one of the X-ray diffraction characteristics of the iron-zinc intermetallic compounds of said steel sheets, said X-ray diffraction characteristics including the X-ray diffraction intensity, the width of the diffraction profile and the peak angle of said diffraction profile, and estimating said degree of alloying on the basis of analysis of said measured X-ray diffraction characteristics.

2. The method as claimed in claim 1 in which measurement of said X-ray diffraction characteristics is applied to said iron-zinc intermetallic compounds at least one of $\zeta$-, $\delta_1$-and $\Gamma$-phases.

3. The method as claimed in claim 2 in which measurement of said X-ray diffraction characteristics is applied to said iron-zinc intermetallic compound of $\zeta$-or $\delta_1$-phase.

4. The method as claimed in claim 1 in which the ordinary parafocusing X-ray beam is used for said diffraction.

5. The method as claimed in claim 1 in which a parallel X-ray beam is used for said diffraction.

6. The method as claimed in claim 1 in which a crystal lattice plane whose $2\theta$ value is 80° or larger is used as the diffraction plane.

7. The method as claimed in claim 1 in which two or more X-ray diffraction characteristics are measured and their combination is used for the estimation.

8. The method as claimed in claim 1 in which the half-value width is used as representative of said width of said X-ray diffraction profile.

9. The method as claimed in claim 1 in which a width of from ⅓ to 1/5 is used as a representative of said width of said X-ray diffraction profile.

* * * * *